US008759536B2

(12) United States Patent
You et al.

(10) Patent No.: US 8,759,536 B2
(45) Date of Patent: Jun. 24, 2014

(54) RHODANINE DERIVATIVES, METHOD FOR PREPARING SAME, AND PHARMACEUTICAL COMPOSITION FOR THE PREVENTION OR TREATMENT OF AIDS CONTAINING THE RHODANINE DERIVATIVES AS ACTIVE INGREDIENTS

(75) Inventors: Ji Chang You, Seoul (KR); Gyoon Hee Han, Hwaseong-si (KR); Chul Ho Lee, Seoul (KR); Doo Na Song, Seoul (KR); Koo Hwan Chung, Seoul (KR)

(73) Assignee: Avixgen Inc., Seoul (KR)

( * ) Notice: Subject to any disclaimer, the term of this patent is extended or adjusted under 35 U.S.C. 154(b) by 0 days.

(21) Appl. No.: 13/805,326

(22) PCT Filed: Jun. 17, 2011

(86) PCT No.: PCT/KR2011/004445
§ 371 (c)(1),
(2), (4) Date: Dec. 18, 2012

(87) PCT Pub. No.: WO2011/159129
PCT Pub. Date: Dec. 22, 2011

(65) Prior Publication Data
US 2013/0096125 A1  Apr. 18, 2013

(30) Foreign Application Priority Data
Jun. 18, 2010  (KR) ........................ 10-2010-0057967

(51) Int. Cl.
*A61K 31/427* (2006.01)
*C07D 417/06* (2006.01)
*C07D 417/14* (2006.01)

(52) U.S. Cl.
USPC ........ 548/183; 514/231.2; 514/369; 544/133; 548/181

(58) Field of Classification Search
USPC ........................................ 548/183
See application file for complete search history.

(56) References Cited

U.S. PATENT DOCUMENTS

| 7,566,732 B2 | 7/2009 | Singh et al. |
| 7,718,680 B2 * | 5/2010 | Pellecchia et al. ............ 514/369 |
| 2004/0009526 A1 | 1/2004 | Yu et al. |
| 2004/0214872 A1 | 10/2004 | Suto et al. |
| 2005/0042213 A1 | 2/2005 | Gelder et al. |
| 2008/0033025 A1 | 2/2008 | Pellecchia et al. |
| 2009/0088420 A1 | 4/2009 | Neamati et al. |
| 2009/0137644 A1 | 5/2009 | Singh et al. |
| 2010/0286212 A1 | 11/2010 | Luo et al. |

FOREIGN PATENT DOCUMENTS

| JP | 07-70095 A | 3/1995 |
| KR | 10-2001-0099623 A | 11/2001 |
| KR | 10-2007-0074250 A | 7/2007 |
| WO | 00/32598 A1 | 6/2000 |
| WO | 2004/028535 A1 | 4/2004 |
| WO | 2005/016227 A2 | 2/2005 |
| WO | 2005/041951 A2 | 5/2005 |
| WO | 2009/059243 A1 | 5/2009 |
| WO | 2009059243 A1 | 5/2009 |
| WO | 2011/050211 A2 | 4/2011 |
| WO | 2011/063602 A1 | 6/2011 |

OTHER PUBLICATIONS

Chemical Registry No. 866256-97-5, indexed in the Registry file on STN CAS Online on Oct. 27, 2005.*
Chemical Registry No. 865578-62-7, indexed in the Registry file on STN CAS Online on Oct. 19, 2005.*
Chemical Registry No. 863113-90-0, indexed in the Registry file on STN CAS Online on Sep. 14, 2005.*
Chemical Registry No. 697784-39-7, indexed in the Registry file on STN CAS Online on Jun. 23, 2004.*
Chemical Registry No. 344897-44-5, indexed in the Registry file on STN CAS Online on Jul. 8, 2001.*
Chemical Registry No. 392717-15-6, indexed in the Registry file on STN CAS Online on Feb. 15, 2002.*
Chemical Registry No. 324070-79-3, indexed in the Registry file on STN CAS Online on Feb. 26, 2001.*
Chemical Registry No. 314076-40-9, indexed in the Registry file on STN CAS Online on Jan. 16, 2001.*
Chemical Registry No. 309945-74-2, indexed in the Registry file on STN CAS Online on Dec. 20, 2000.*
Chemical Registry No. 324543-78-4, indexed in the Registry file on STN CAS Online on Feb. 27, 2001.*
Chemical Registry No. 292076-10-9, indexed in the Registry file on STN CAS Online on Oct. 2, 2000.*
Chemical Registry No. 324544-03-8, indexed in the Registry file on STN CAS Online on Feb. 27, 2001.*
Chemical Registry No. 327054-35-3, indexed in the Registry file on STN CAS Online on Mar. 14, 2001.*
Chemical Registry No. 302934-44-7, indexed in the Registry file on STN CAS Online on Nov. 15, 2000.*
Chemical Registry No. 330985-84-7, indexed in the Registry file on STN CAS Online on Apr. 12, 2001.*
Chemical Registry No. 344896-92-0, indexed in the Registry file on STN CAS Online on Jul. 8, 2001.*

(Continued)

*Primary Examiner* — Laura L. Stockton
(74) *Attorney, Agent, or Firm* — Knobbe, Martens, Olson & Bear, LLP

(57) ABSTRACT

Disclosed are novel rhodanine derivatives which are inhibitory of HIV activity. Also provided are a method for preparing the novel rhodanine derivatives, and a pharmaceutical composition for the prevention or treatment of AIDS containing the rhodanine derivatives as active ingredients. Having high inhibitory activity against HIV, the rhodanine derivatives can be effectively used in the prophylaxis or therapy of AIDS.

15 Claims, No Drawings

(56) References Cited

OTHER PUBLICATIONS

Chemical Registry No. 341959-96-4, indexed in the Registry file on STN CAS Online on Jun. 17, 2001.*
Chemical Registry No. 327033-20-5, indexed in the Registry file on STN CAS Online on Mar. 14, 2001.*
Huff, Journal of Medicinal Chemistry, 34(8), 1991, pp. 2305-2314.*
Chemical Registry No. 312497-24-8, indexed in the Registry file on STN CAS Online on Jan. 2, 2001.*
Chemical Registry No. 292173-76-3, indexed in the Registry file on STN CAS Online on Oct. 3, 2000.*
Chapman et al., Antiviral Research, 54, (2002), pp. 149-162.*
Notice of Allowance issued on Jun. 11, 2012 for Korean Application No. 10-2010-0057967, in 5 pages.
International Search Report issued on Feb. 15, 2012 for International Application No. PCT/KR2011/004445.
Supplementary European Search Report dated Sep. 24, 2013 of the corresponding European Patent Application No. 11795995.7—8 pages.

* cited by examiner

RHODANINE DERIVATIVES, METHOD FOR PREPARING SAME, AND PHARMACEUTICAL COMPOSITION FOR THE PREVENTION OR TREATMENT OF AIDS CONTAINING THE RHODANINE DERIVATIVES AS ACTIVE INGREDIENTS

TECHNICAL FIELD

The present invention relates to a novel rhodanine derivative, a method for preparing the same, and a pharmaceutical composition for the prevention or treatment of AIDS, comprising the same as an active ingredient.

BACKGROUND ART

AIDS was first clinically observed in 1981, and HIV (Human Immunodeficiency Virus) was discovered as causing AIDS as it was isolated from AIDS patients in 1984.

Taxonomically, HIV is a member of the genus *Lentivirus*, part of the family of Retroviridae. An HIV particle is roughly spherical with a diameter of about 10 microns. Its genome is composed of two copies of RNA enclosed by a protein sac (capsid, core protein) which is, in turn, surrounded by a viral envelope composed of phospholipids, like general plasma membranes. The HIV genome codes for 10 genes, which are too many relative to the total size of the genome.

HIV infection is mediated through interaction of the envelope glycoproteins (gp120) on the viral surface with receptors on the target cell. The cell surface protein molecules that act as the receptors are mainly CD4 antigens. This is why cells that express CD4 on their surface (CD4+ cells), such as macrophages and helper T cells, are the main target cells of HIV. Following the adsorption of the glycoprotein to the receptors, the viral phospholipid envelope is fused with the cell membrane with the concomitant release of the HIV genome and nucleocapsid into the cell. Upon entry into the target cell, the viral RNA genome is converted into DNA by a virally encoded reverse transcriptase that is transported along with the viral genome in the virus particle. The viral DNA is then transported into the cell nucleus and integrated into the host cell's genome. This procedure is one of the unique features that retroviruses have. As such, the integrated viral DNA lies dormant in the safest site of the host cell while being supplied with all mechanisms and resources necessary for the growth of the virus from the cell. Further, HIV protects itself from and survives the immune system while proliferating or entering the latent stage of infection depending on surrounding situations and conditions.

Two types of AIDS viruses are characterized: HIV-1 and HIV-2. HIV-1 is found in patients all over the world and is the cause of the majority of HIV infections globally. HIV-2 is largely confined to West Africa. Its nucleotide sequence is only 55% identical to that of HIV-1, and rather more similar to that of SIV (Simian Immunodeficiency Virus), known as monkey AIDS virus. HIV-2 is less virulent than HIV-1. HIV not only has very high biological variability, but also very high genetic variability. The nucleotide sequences of HIV differ from one AIDS patient to another, and vary with the progress of AIDS even in the same patient. What is more serious, the nucleotide sequences of HIV, when sampled at the same time from the same patient, are different depending on sampling tissue. These HIV sequence polymorphisms are strongly associated with various biological characteristics of the virus. Given different nucleotide sequences, HIV differs in target cell preference for its infection, virion productivity, cytotoxicity, ability to form multinucleated giant cells, latent period and active period, and sensitivity to neutralizing antibodies. More recent studies on the relationship between variable biological properties of HIV and pathogenesis of HIV infection show that most AIDS viruses isolated from patients in the early stages do not create multinucleated giant cells (nonsyncytia-inducing (NSI)) and prefer macrophages for their infection, whereas HIV is increasingly liable to create multinucleated giant cells (syncytia-inducing (SI)), and replicate preferably in T-helper cells, with the progression of AIDS, indicating that there is strong relationship between biological properties of HIV and pathogenesis of HIV infection.

One week after HIV infection, the virus actively proliferates and can be easily detected in the blood of the infectee, that is, he or she becomes viremic. Then, the virus rapidly decreases to such a low level within one to two weeks that it cannot be isolated. After maintenance of such latency for a significant period of time, HIV actively replicates with the onset of AIDS, so that viremia occurs. Recent PCR research has attracted attention because of its report that HIV replicates while it is dormant. After HIV infection, the level of CD4 cells rapidly decreases during the primary viremia period, and then is recovered to a constant value (healthy person: 500-1000 CD4 cells/mm$^2$). Since that point, the blood level of CD4 cells gradually decreases over several years. When CD4 cells drop below 200 counts per mm$^3$ of blood, the onset of ARC (AIDS-related complex) or AIDS takes place. AIDS patients experience a condition in which progressive failure of the immune system allows life-threatening opportunistic infections, such as *Pneumocysitis carinii* pneumonia, to thrive. The time period during which the HIV level rapidly reduces after the primary viremia is incident with the activation period of CD8 cells. CD8 T cells are known to act to inhibit cell growth or selectively kill virus-infected cells. Hence, CD8 T cells seem to account for immunity against the early infection virus. Antibodies are produced after the virus level is reduced. CD8 cells and antibodies continue to exist during the time period from the initial time of infection to the onset of AIDS, but their functions have been reduced, or denatured, and they even promote the HIV infection. How the immune system that exhibits apparent anti-viral activity in the early stage of infection is lost remains a problem that is yet to be solved. Due to AIDS specificity for humans, the understanding of the etiology of HIV is at an extremely low level. Although there is consensus among scientists about the fact that a reduction in CD4 cell level is a direct cause of immunodeficiency, there are various different opinions on how HIV reduces the level of CD4 cells. Suggested theories accounting for the reduction of CD4 cell level include the formation of multinucleated giant cells, the accumulation of non-inserted viral DNA, influence on the structure of host cell membranes, the induction of programmed cell death, the secretion of toxic matter from infected cells, and autoimmune-mediated cytolysis. None of them, however, have thus far been proven as fact, or have been shown to occur in practice in vivo. Extensive research into HIV pathogenesis has been conducted on monkeys using the monkey AIDS virus SIV, but it has yielded no novel findings.

Most prevalent among currently available AIDS drugs is AZT (zidovudine), which is an HIV reverse transcriptase inhibitor. It remains in widespread use today and is recognized as one of the most effective drugs in medical history. This drug is clinically very effective in the early stages of HIV infection, but is found to have no positive influences on the extension of a patient's life because of its side effects. That is, AZT induces bone marrow toxicity, and may allow HIV to become AZT-resistant over time. DDI, DDC, and d4T, all functioning like AZT, and approved by the FDA, are found to be less toxic than AZT, but induce HIV to be resistant thereto.

There are many anti-viral methods that have been developed that are awaiting efficacy testing. Examples of them are the prevention of viral adsorption to cells, the selective killing of virus-infected cells, the use of inhibitors against enzymes playing an important role in viral growth (e.g., protease, integrase, tat inhibitor, rev inhibitor, etc.), cytokine therapies, injection of CD8 cells, and gene therapies. There has also been a great advance in the development of HIV vaccines, such as the use of a dead virus, or attenuated virus, which is alive but not pathogenic, an isolated viral protein expressed by bioengineering (subunit vaccine), an anti-idiotypic antibody, and the direct injection of a DNA gene. However, a fundamental problem with the development of vaccines lies in the excessive diversity of HIV viruses. For example, a person immunized with a vaccine is observed to inhibit the virus used for developing the vaccine when challenged with the same virus, but does not exhibit immunoprotection at all when challenged with the infected cells or viruses taken from a different patient. This viral diversity also remains as a problem yet to be solved.

There is therefore a pressing need for an AIDS drug that overcomes the problems encountered in the prior arts, including side effects and resistant viruses of conventional AIDS therapeutics.

DISCLOSURE

Technical Problem

Leading to the present invention, intensive and thorough research into AIDS therapy, conducted by the present inventors, resulted in the finding that novel rhodanine derivatives have excellent inhibitory activity against HIV, without side effects or the induction of resistant viruses.

Technical Solution

The present invention is to provide a novel rhodanine derivative, a method for preparing the same, and a pharmaceutical composition for the prophylaxis or therapy of AIDS, comprising the same as an active ingredient.

Advantageous Effects

Exhibiting excellent anti-HIV activity by inhibiting HIV expression, the rhodanine derivatives of the present invention are useful in the prophylaxis or therapy of AIDS.

BEST MODE

In accordance with an aspect thereof, the present invention addresses a rhodanine derivative selected from the group consisting of:
3-(2,4-dimethyl-phenyl)-5-[5-(3-nitro-phenyl)-furan-2-ylmethylene]-2-thioxo-thiazolidin-4-one,
5-[5-(4-morpholin-4-yl-3-nitro-phenyl)-furan-2-ylmethylene]-2-thioxo-thiazolidin-4-one,
5-[5-(4-oxo-2-thioxo-thiazolidin-5-ylidene methyl)-furan-2-yl]-isoindole-1,3-dione,
3-(2-methanesulfonyl-ethyl)-5-[5-(3-nitro-phenyl)-furan-2-ylmethylene]-2-thioxo-thiazolidin-4-one,
5-[5-(4-bromo-phenyl)-furan-2-ylmethylene]-3-(3-oxo-butyl)-2-thioxo-thiazolidin-4-one,
5-[5-(4-nitro-phenyl)-furan-2-ylmethylene]-3-(tetrahydro-furan-2-ylmethyl)-2-thioxo-thiazolidin-4-one,
3-(4-diethylamino-phenyl)-5-[5-(4-nitro-phenyl)-furan-2-ylmethylene]-2-thioxo-thiazolidin-4-one,
5-[5-(2,4-dichloro-phenyl)-furan-2-ylmethylene]-3-(3-fluoro-phenyl)-2-thioxo-thiazolidin-4-one,
3-phenethyl-5-(5-phenyl-furan-2-ylmethylene)-2-thioxo-thiazolidin-4-one,
5-[5-(3-chloro-4-methyl-phenyl)-furan-2-ylmethylene]-3-ethyl-2-thioxo-thiazolidin-4-one,
5-(naphthalen-1-yl-furan-2-ylmethylene)-3-(2-oxo-propyl)-2-thioxo-thiazolidin-4-one,
3-cyclohexyl-5-[5-(2-nitro-phenyl)-furan-2-ylmethylene]-2-thioxo-thiazolidin-4-one,
3-(3-fluoro-phenyl)-5-[5-(4-nitro-phenyl)-furan-2-ylmethylene]-2-thioxo-thiazolidin-4-one,
3-(1,1-dioxo-tetrahydro-thiopen-3-yl)-5-[5-(2-nitro-phenyl)-furan-2-ylmethylene]-2-thioxo-thiazolidin-4-one,
5-[5-(2-nitro-phenyl)-furan-2-ylmethylene]-3-(4-oxo-pentyl)-2-thioxo-thiazolidin-4-one,
5-[5-(2-bromo-5-nitro-phenyl)-furan-2-ylmethylene]-3-(4-iodo-phenyl)-2-thioxo-thiazolidin-4-one,
5-[5-(2-chloro-4-nitro-phenyl)-furan-2-ylmethylene]-2-thioxo-3-(3-trifluoromethyl-phenyl)-thiazolidin-4-one
3-benzyl-5-[5-(4-ethoxy-2-nitro-phenyl)-furan-2-ylmethylene]-2-thioxo-thiazolidin-4-one,
{5-[5-(2-methyl-5-nitro-phenyl)-furan-2-ylmethylene]-4-oxo-2-thioxo-thiazolidin-3-yl}-acetic acid,
{5-[5-(4-ethoxy-2-nitro-phenyl)-furan-2-ylmethylene]-4-oxo-2-thioxo-thiazolidin-3-yl}-acetic acid,
{5-[5-(4-methoxy-2-nitro-phenyl)-furan-2-ylmethylene]-4-oxo-2-thioxo-thiazolidin-3-yl}-acetic acid,
3-(4-nitro-phenyl)-5-[5-(4-nitro-phenyl)-furan-2-ylmethylene]-2-thioxo-thiazolidin-4-one, and
4-[5-(4-oxo-2-thioxo-thiazolidin-5-ylidene methyl)-furan-2-yl]-benzoic acid isopropylester, or a pharmaceutically acceptable salt thereof.

The rhodanine derivatives of the present invention may be prepared into pharmaceutically acceptable salts or solvates using typical methods known in the art.

Within the range of the pharmaceutically acceptable salts are included, for example, acid addition salts formed with pharmaceutically acceptable free acids. The acid addition salts of the compound according to the present invention may be prepared using a conventional method, for example, by dissolving the rhodanine derivative in excess acid in water and precipitating the resulting salt in a water-miscible organic solvent, e.g., methanol, ethanol, acetone or acetonitrile. Alternatively, the rhodanine derivative of the present invention may be heated along with the same molar amount of acid or alcohol (e.g., glycol monomethyl ether) in water, followed by evaporating the mixture and drying or suction filtering the precipitate to prepare acid addition salts thereof.

The free acids may be inorganic or organic. Examples of useful inorganic free acids include hydrochloric acid, phosphoric acid, sulfuric acid, nitric acid, and stannic acid. As organic acids, methane sulfonic acid, p-toluene sulfonic acid, acetic acid, trifluoroacetic acid, citric acid, maleic acid, succinic acid, oxalic acid, benzoic acid, tartaric acid, fumaric acid, mandelic acid, propionic acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid may be used.

Also, metal salts formed with bases may fall within the range of pharmaceutically acceptable salts of the compound of the present invention. Examples of the metal salts useful in the present invention include alkali metal salts and alkaline earth metal salts. By way of example, the compound of the present invention may be dissolved in excess alkali metal hydroxide or alkaline earth metal hydroxide in water, and, after the filtration of the solution to remove non-dissolved compound salts, the filtrate may be dried to afford the pharmaceutically acceptable salts of the compound of the present invention. Suitable for use in pharmaceutics are sodium, potassium or calcium salts. Corresponding silver salts may be obtained by reacting the alkali metal or alkaline earth metal salts with suitable silver salt (e.g., silver nitrate).

Unless otherwise stated, the pharmaceutically acceptable salts of the rhodanine derivatives of the present invention include salts of the acid or base groups present on the rhodanine derivatives. For example, the pharmaceutically acceptable salts include sodium, calcium or potassium salts of hydroxyl groups. For amino groups, hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate) may be exemplified, and can be prepared using a typical method known in the art.

In accordance with another aspect thereof, the present invention addresses a method for preparing a rhodanine derivative, comprising:

1) reacting an amine compound of Chemical Formula 2 with carbon disulfide ($CS_2$) and bromoacetic acid to synthesize a compound of Chemical Formula 3, 2) reacting a halide compound of Chemical Formula 4 with 5-formyl-2-furanboronic acid to synthesize a compound of Chemical Formula 5, and 3) reacting the compound of Chemical Formula 3, synthesized in step 1), with the compound of Chemical Formula 5, synthesized in step 2), to afford a compound of Chemical Formula 1, as illustrated in the following Schematic Scheme 1:

[Reaction Scheme 1]

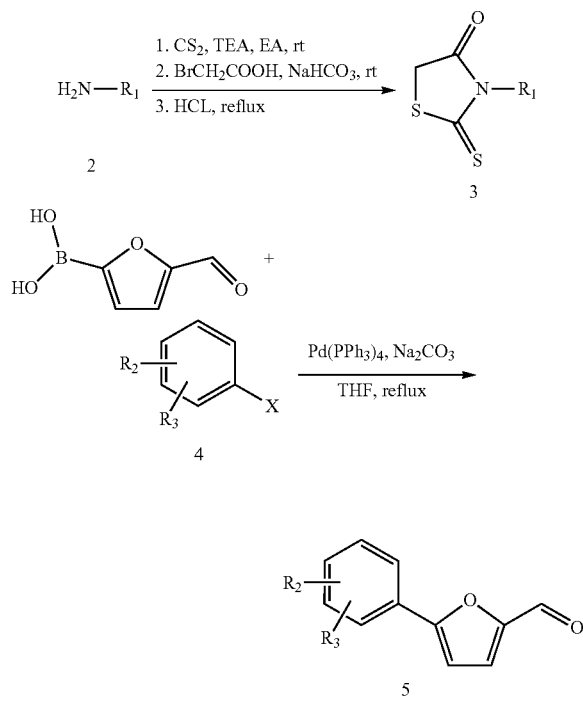

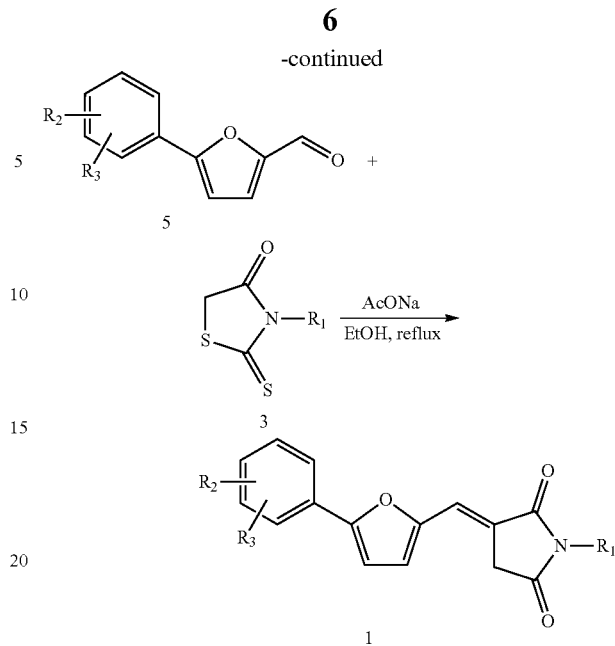

wherein, $R_1$ is H, ethyl, cyclohexyl, —$(CH_2)$n-A-B, —$(CH_2)$m-phenyl, 2,4-dimethylphenyl,

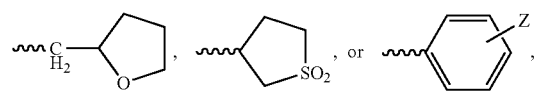

Wherein
A is (C=O) or $SO_2$,
B is methyl or hydroxy,
Z is F, I, $NO_2$, $CF_3$, or —N $(CH_2CH_3)_2$,
n is an integer of 1~3, and
m is an integer of 1 or 2,
$R_2$, and $R_3$, which may be the same or different, are independently H, $NO_2$, Br, Cl, methyl, methoxy, ethoxy, —(C=O)—O—$CH(CH_3)_2$, or morpholine, or $R_2$ and $R_3$ are positioned ortho to each other, joining together to form

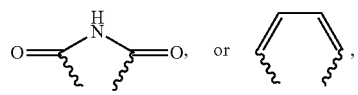

and
X is a halogen atom.

In accordance with a further aspect thereof, the present invention provides a method of preventing or treating AIDS comprising administering a rhodanine derivative selected from the group consisting of:

3-(2,4-dimethyl-phenyl)-5-[5-(3-nitro-phenyl)-furan-2-ylmethylene]-2-thioxo-thiazolidin-4-one,
5-[5-(4-morpholin-4-yl-3-nitro-phenyl)-furan-2-ylmethylene]-2-thioxo-thiazolidin-4-one,
5-[5-(4-oxo-2-thioxo-thiazolidin-5-ylidene methyl)-furan-2-yl]-isoindole-1,3-dione,
3-(2-methanesulfonyl-ethyl)-5-[5-(3-nitro-phenyl)-furan-2-ylmethylene]-2-thioxo-thiazolidin-4-one,
5-[5-(4-bromo-phenyl)-furan-2-ylmethylene]-3-(3-oxo-butyl)-2-thioxo-thiazolidin-4-one, 5-[5-(4-nitro-phenyl)-furan-2-ylmethylene]-3-(tetrahydro-furan-2-ylmethyl)-2-thioxo-thiazolidin-4-one,
3-(4-diethylamino-phenyl)-5-[5-(4-nitro-phenyl)-furan-2-ylmethylene]-2-thioxo-thiazolidin-4-one,
5-[5-(2,4-dichloro-phenyl)-furan-2-ylmethylene]-3-(3-fluoro-phenyl)-2-thioxo-thiazolidin-4-one,
3-phenethyl-5-(5-phenyl-furan-2-ylmethylene)-2-thioxo-thiazolidin-4-one,
5-[5-(3-chloro-4-methyl-phenyl)-furan-2-ylmethylene]-3-ethyl-2-thioxo-thiazolidin-4-one,
5-(naphthalen-1-yl-furan-2-ylmethylene)-3-(2-oxo-propyl)-2-thioxo-thiazolidin-4-one,
3-cyclohexyl-5-[5-(2-nitro-phenyl)-furan-2-ylmethylene]-2-thioxo-thiazolidin-4-one,
3-(3-fluoro-phenyl)-5-[5-(4-nitro-phenyl)-furan-2-ylmethylene]-2-thioxo-thiazolidin-4-one,
3-(1,1-dioxo-tetrahydro-thiopen-3-yl)-5-[5-(2-nitro-phenyl)-furan-2-ylmethylene]-2-thioxo-thiazolidin-4-one,
5-[5-(2-nitro-phenyl)-furan-2-ylmethylene]-3-(4-oxo-pentyl)-2-thioxo-thiazolidin-4-one,
5-[5-(2-bromo-5-nitro-phenyl)-furan-2-ylmethylene]-3-(4-iodo-phenyl)-2-thioxo-thiazolidin-4-one,
5-[5-(2-chloro-4-nitro-phenyl)-furan-2-ylmethylene]-2-thioxo-3-(3-trifluoromethyl-phenyl)-thiazolidin-4-one,
3-benzyl-5-[5-(4-ethoxy-2-nitro-phenyl)-furan-2-ylmethylene]-2-thioxo-thiazolidin-4-one,
{5-[5-(2-methyl-5-nitro-phenyl)-furan-2-ylmethylene]-4-oxo-2-thioxo-thiazolidin-3-yl}-acetic acid,
{5-[5-(4-ethoxy-2-nitro-phenyl)-furan-2-ylmethylene]-4-oxo-2-thioxo-thiazolidin-3-yl}-acetic acid,
{5-[5-(4-methoxy-2-nitro-phenyl)-furan-2-ylmethylene]-4-oxo-2-thioxo-thiazolidin-3-yl}-acetic acid,
3-(4-nitro-phenyl)-5-[5-(4-nitro-phenyl)-furan-2-ylmethylene]-2-thioxo-thiazolidin-4-one,
4-[5-(4-oxo-2-thioxo-thiazolidin-5-ylidene methyl)-furan-2-yl]-benzoic acid isopropylester,
5-[5-(2,5-dichloro-phenyl)-furan-2-ylmethylene]-3-(1,5-dimethyl-3-oxo-2-phenyl-2,3-dihydro-1H-pyrazol-4-yl)-2-thioxo-thiazolidin-4-one,
5-[5-(1-oxo-1,3-dihydro-isobenzofuran-5-yl)-furan-2-ylmethylene-2-thioxo-thiazolidin-4-one,
3-furan-2-ylmethyl-5-[5-(2-nitro-phenyl)-furan-2-ylmethylene]-2-thioxo-thiazolidin-4-one,
5-[5-(2-nitro-phenyl)-furan-2-ylmethylene]-3-phenethyl-2-thioxo-thiazolidin-4-one,
3-(3-chloro-phenyl)-5-[5-(2,3-dichloro-phenyl)-furan-2-ylmethylene]-2-thioxo-thiazolidin-4-one,
2-chloro-5-[5-(4-oxo-2-thioxo-thiazolidin-5-ylidene methyl)-furan-2-yl]-benzoic acid propyl ester,
4-{5-[5-(3,4-dichloro-phenyl)-furan-2-ylmethylene]-4-oxo-2-thioxo-thiazolidin-3-yl}-butyric acid,
2-{5-[5-(4-nitro-phenyl)-furan-2-ylmethylene]-4-oxo-2-thioxo-thiazolidin-3-yl}-succinic acid,
5-[5-(4-chloro-phenyl)-furan-2-ylmethylene]-3-furan-2-ylmethyl-2-thioxo-thiazolidin-4-one,
5-[5-(2,4-dichloro-phenyl)-furan-2-ylmethylene]-2-thioxo-3-(3-trifluoromethyl-phenyl)-thiazolidin-4-one,
3-furan-2-ylmethyl-5-[5-(4-nitro-phenyl)-furan-2-ylmethylene]-2-thioxo-thiazolidin-4-one,
3-{5-[5-(3-nitro-phenyl)-furan-2-ylmethylene]-4-oxo-2-thioxo-thiazolidin-3-yl}-propionic acid,
3-{5-[5-(4-chloro-phenyl)-furan-2-ylmethylene]-4-oxo-2-thioxo-thiazolidin-3-yl}-propionic acid,
4-{5-[3-(2,4-dimethyl-phenyl)-4-oxo-2-thioxo-thiazolidin-5-ylidene methyl]-furan-2-yl}-benzoic acid, and
{5-[5-(3-nitro-phenyl)-furan-2-ylmethylene]-4-oxo-2-thioxo-thiazolidin-3-yl}-acetic acid.

The compounds of the present invention exhibit excellent anti-HIV activity by inhibiting HIV viral expression. Hence, the rhodanine derivatives of the present invention may be useful for preventing or treating AIDS.

The composition of the present invention may further comprise at least one active ingredient known for inhibitory activity against HIV, in addition to the rhodanine derivative.

For administration, the pharmaceutical composition may further comprise a pharmaceutically acceptable carrier, in addition to the active ingredients. Examples of the pharmaceutically acceptable carrier include saline, sterile water, Ringer's solution, buffered saline, a dextrose solution, a maltodextrin solution, glycerol, ethanol, etc. Optionally, typical additives, such as antioxidants, buffers, bacteriostatic agents, etc., may be added to the composition. For the preparation of dosage forms including injections, such as aqueous solutions, suspensions and emulsions, pills, capsules, granules and tablets, the active ingredients may be admixed with a diluent, a dispersant, a surfactant, a binder and/or a lubricant. Reference may be made to literature (Remington's Pharmaceutical Science (latest edition), Mack Publishing Company, Easton Pa.) regarding the formulation of the pharmaceutical composition into suitable dosage forms.

The composition of the present invention may be administered via oral routes or parenteral routes (e.g., intravenous, subcutaneous, intraperitoneal, topical, etc.). The effective dosage of the inhibitor in accordance with the present invention depends on various factors, including the patient's weight, age, gender, state of health, diet, the time of administration, the route of administration, excretion rate, severity of diseases, etc. In general, the rhodanine derivative may be administered in a single dose, and preferably in multiple doses per day at a daily dose ranging from 0.1 to 50 mg/day, and preferably from 2 to 10 mg/kg.

For the effective prophylaxis and therapy of AIDS, the composition according to the present invention may be used alone or in combination with surgical operation, hormonal therapy, a drug, and/or biological response controllers.

A better understanding of the present invention may be obtained through the following examples which are set forth to illustrate, but are not to be construed as limiting the present invention.

Example 1

Preparation of 3-(2,4-Dimethyl-phenyl)-5-[5-(3-nitro-phenyl)-furan-2-ylmethylene]-2-thioxo-thiazolidin-4-one 1. Synthesis of 3-(2,4-dimethyl-phenyl)-2-thioxo-thiazolidin-4-one

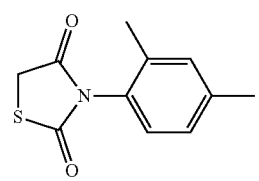

At 0° C., 1 g of 2,4-dimethylaniline (8.04 mmol) was mixed with 54 mL of a 0.2 M solution of triethylamine in ethyl acetate, and 0.65 mL of a carbon disulfide ($CS_2$) solution was dropwise added to the mixture with slowly stirring. After completion of the addition, stirring was continued for an additional 12 hrs. The reaction mixture was filtered, and the filtrate was dissolved in an aqueous sodium bicarbonate solution (NaHCO₃) and mixed with 2.2. g of bromoacetic acid (15.83 mmol) for 2 hrs by stirring. The resulting reaction mixture was acidified (pH 2) with a 35% HCl solution and heated for 6 hrs. After extraction with methylene chloride (CH₂Cl₂), the organic layer was pooled, washed with saturated brine, dried over magnesium sulfate, and concentrated in vacuo. Purification of the concentrate by silica gel column chromatography afforded the title compound.

1-1. Alternative synthesis of 3-(2,4-dimethyl-phenyl)-2-thioxo-thiazolidin-4-one To a solution of 1 g of 2,4-dimethylaniline (8.04 mmol) in 8.9 mL of 22% KOH was dropwise added 0.81 mL of carbon dioxide, with stirring. After completion of the addition, stirring was continued for an additional 12 hrs. The solution was mixed for 2 hrs with 2.78 g of bromoacetic acid (20.01 mmol), with stirring. Then, the reaction mixture was acidified with sulfuric acid, stirred at room temperature for 12 hrs, and washed with water to afford the title compound.

2. Synthesis of 5-(3-nitro-phenyl)-furan-2-carboaldehyde

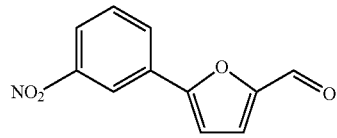 [SMILES: O=Cc1ccc(-c2cccc([N+](=O)[O-])c2)o1]

To a mixture of 1.5 g of 1-bromo-3-nitrobenzene (7.42 mmol), 1 g of 5-formyl-2-furanboronic acid (7.42 mmol), and 35 mL of a solution of saturated sodium carbonate (Na₂CO₃) in 0.2 M tetrahydrofuran was added 0.2 g of tetrakis triphenylphosphine palladium [Pd(PPh₃)₄] (0.2 mmol) at room temperature with stirring. After completion of the addition, the resulting mixture was heated for an additional 12 hrs, cooled to room temperature, and concentrated in vacuo. The concentrate was extracted with methylene chloride, and the organic layer thus formed was added, washed with saturated brine, dried over magnesium sulfate, and concentrated in a vacuum. Purification by silica gel column chromatography afforded the title compound.

3. Synthesis of 3-(2,4-dimethyl-phenyl)-5-[5-(3-nitro-phenyl)-furan-2-ylmethylene]-2-thioxo-thiazolidin-4-one

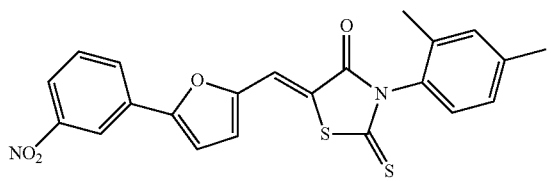 [SMILES: Cc1ccc(N2C(=O)/C(=C/c3ccc(-c4cccc([N+](=O)[O-])c4)o3)SC2=S)c(C)c1]

In 4.7 mL of 0.2 M ethanol was dissolved 0.1 g of 3-(2,4-dimethyl-phenyl)-2-thioxo-thiazolidin-4-one (0.42 mmol) synthesized in 1. The solution was mixed with 0.11 g of sodium acetate (1.34 mmol) and 0.15 g of 5-(3-nitro-phenyl)-furan-2-carboaldehyde (0.69 mmol), synthesized in 2, with stirring, and then heated for 4 hrs. The resulting reaction mixture was washed with ethanol to afford the title compound as a solid. When a solid was not formed, purification by silica gel column chromatography afforded 0.54 g of the title compound (yield: 28.6%).

ESI(m/z): 437(M⁺)

¹H NMR (500 MHz, DMSO): 8.66-8.65 (d, J=5 Hz, 1H), 8.30-8.26 (m, 1H), 7.88 (t, J=8 Hz, 1H), 7.79-7.77 (d, J=10 Hz, 1H), 7.64 (t, J=5.3 Hz, 1H), 7.44 (t, J=5 Hz, 1H), 7.24-7.15 (m, 3H), 2.35-2.33 (d, J=10 Hz, 3H), 2.02-2.00 (d, J=10 Hz, 3H)

Examples: 2 to 23

The same procedure as in reaction scheme 1 was carried out to prepare compounds of Examples 2 to 23.

In Table 1, structural formulas, MS data, and ¹H NMR data of the compounds of Examples 2 to 23 are summarized.

TABLE 1

| Example | Structure | LC-MS (M⁺ H) data or ¹H NMR data |
|---|---|---|
| 2 | 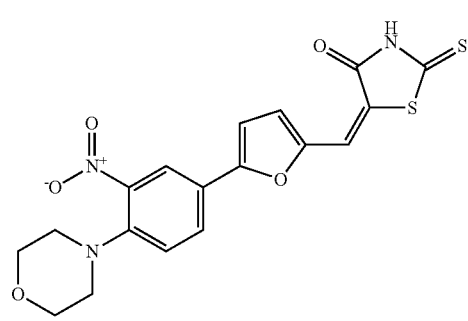 | ESI (m/z): 418(M⁺) |

TABLE 1-continued

| Example | Structure | LC-MS (M+ H) data or <br> ¹H NMR data |
|---|---|---|
| 3 | 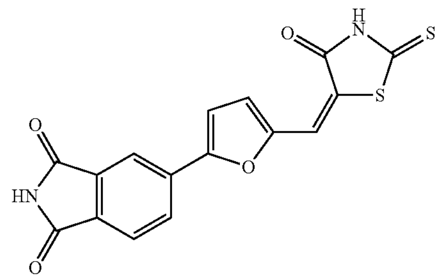 [SMILES: O=C1NC(=S)S/C1=C/c1ccc(-c2ccc3c(c2)C(=O)NC3=O)o1] | ESI (m/z): 357(M+) |
| 4 | 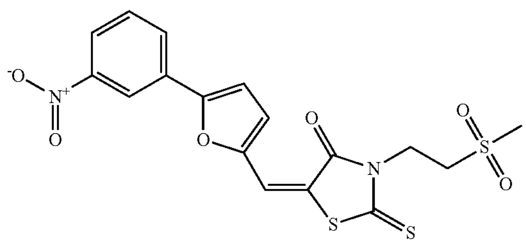 | ESI (m/z): 441(M+) |
| 5 | 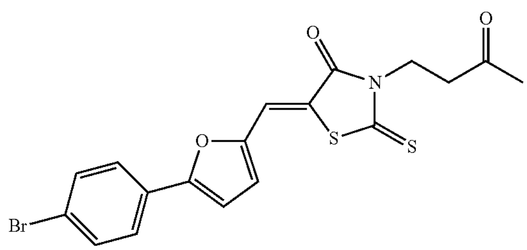 | ESI (m/z): 439 (M+) |
| 6 | 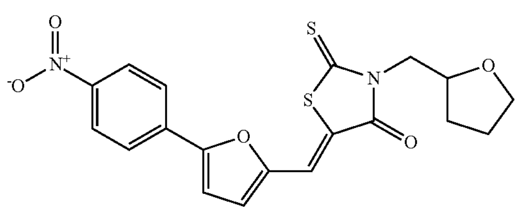 | ESI (m/z): 401(M+) <br> ³H NMR (500 MHz. DMSO): 8.43-8.41 (m, 2H), 8.10-8.08(m, 2H), 2.24(s, 1H), 7.64(d, J = 4.0 MHZ, 1H), 7.44(d, J = 4.0 MHZ, 1H), 4.33-4.29(m, 1H), 4.17-4.13(m, 1H), 4.00-3.97(m, 1H), 3.78-3.73(m, 1H), 3.65-3.61(m, 1H), 1.95-1.90(m, 2H), 1.82-1.68(m, 2H) |
| 7 | 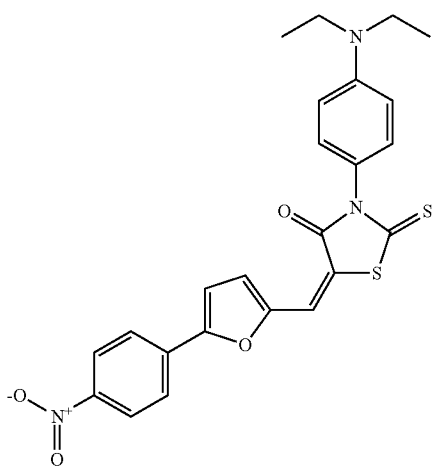 | ESI (m/z): 480(M+) |

TABLE 1-continued

| Example | Structure | LC-MS (M+ H) data or <br> 1H NMR data |
|---------|-----------|----------------------------------------|
| 8 | 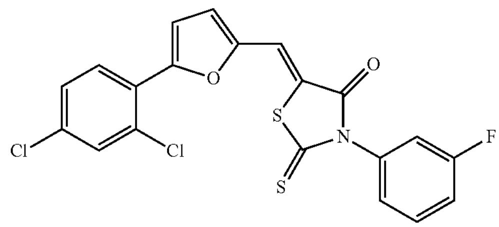 [SMILES: O=C1/C(=C/c2ccc(-c3ccc(Cl)cc3Cl)o2)SC(=S)N1c1cccc(F)c1] | ESI (m/z): 451(M+) |
| 9 | 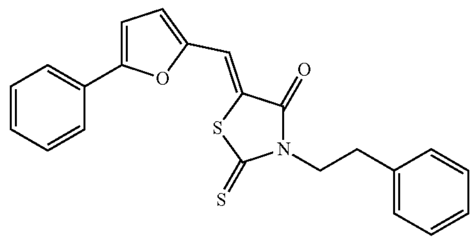 [SMILES: O=C1/C(=C/c2ccc(-c3ccccc3)o2)SC(=S)N1CCc1ccccc1] | ESI (m/z): 392(M+) |
| 10 | 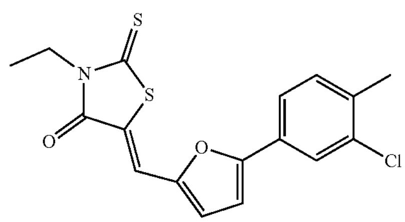 [SMILES: CCN1C(=O)/C(=C/c2ccc(-c3ccc(C)c(Cl)c3)o2)SC1=S] | ESI (m/z): 364(M+) |
| 11 | 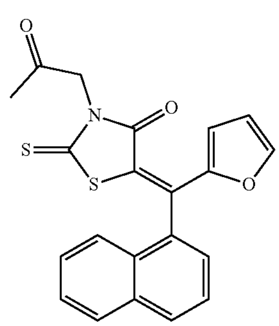 [SMILES: CC(=O)CN1C(=O)/C(=C(\c2ccco2)c2cccc3ccccc23)SC1=S] | ESI (m/z): 396(M+) |
| 12 | 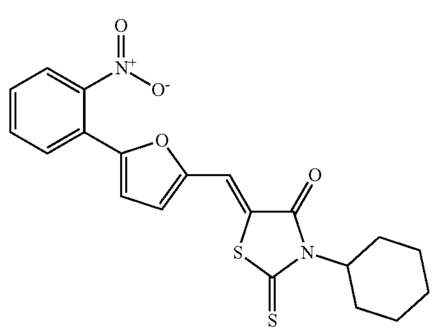 [SMILES: O=C1/C(=C/c2ccc(-c3ccccc3[N+](=O)[O-])o2)SC(=S)N1C1CCCCC1] | ESI (m/z): 415(M+) |

TABLE 1-continued

| Example | Structure | LC-MS (M+ H) data or ¹H NMR data |
|---|---|---|
| 13 | 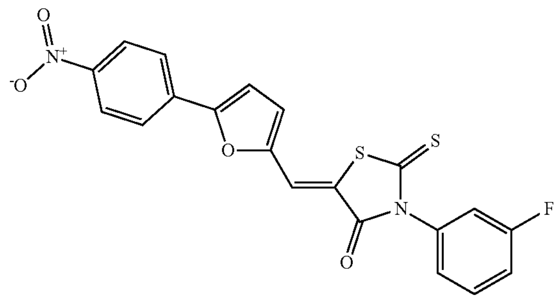 | ESI (m/z): 427(M+) |
| 14 | 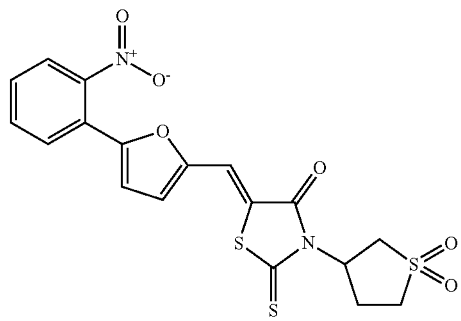 [SMILES: O=C1/C(=C/c2ccc(-c3ccccc3[N+](=O)[O-])o2)SC(=S)N1C1CCS(=O)(=O)C1] | ESI (m/z): 451(M+) |
| 15 | 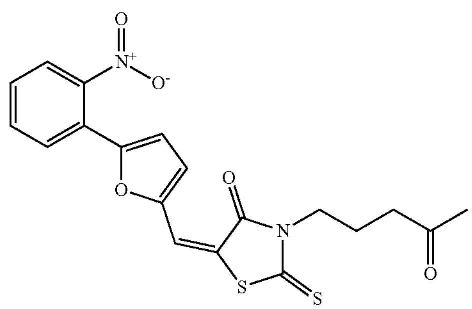 [SMILES: CC(=O)CCCN1C(=O)/C(=C\c2ccc(-c3ccccc3[N+](=O)[O-])o2)SC1=S] | ESI (m/z): 419(M+) |
| 16 | 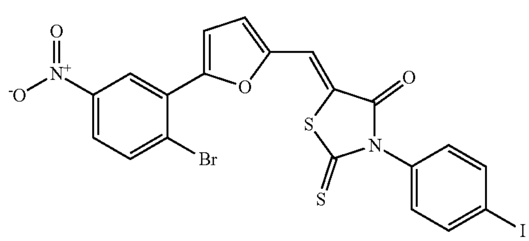 | ESI (m/z): 614(M+) |
| 17 | 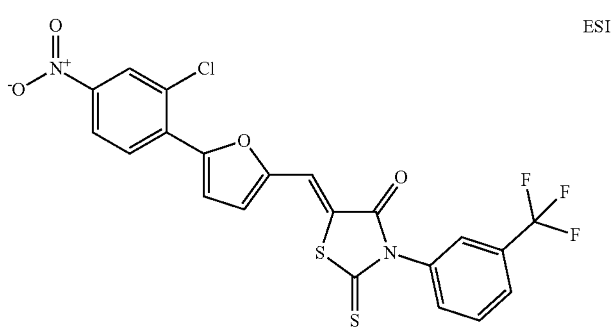 | ESI (m/z): 511(M+) |

TABLE 1-continued

| Example | Structure | LC-MS (M+ H) data or $^1$H NMR data |
|---|---|---|
| 18 | 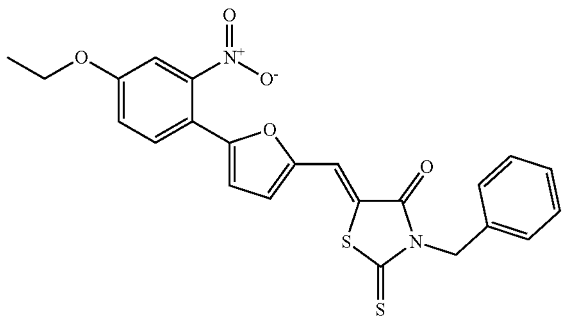 [SMILES: CCOc1ccc(-c2ccc(/C=C3\SC(=S)N(Cc4ccccc4)C3=O)o2)c([N+](=O)[O-])c1] | ESI (m/z): 467(M+) |
| 19 | 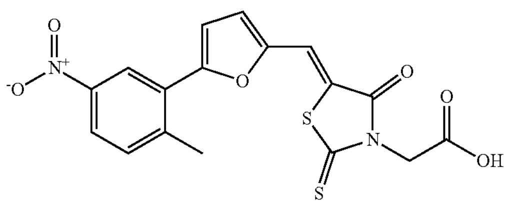 | ESI (m/z): 405(M+) |
| 20 | 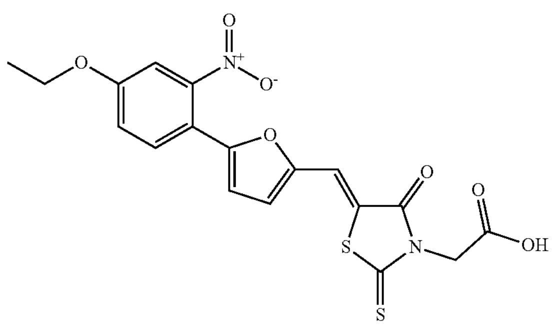 [SMILES: CCOc1ccc(-c2ccc(/C=C3\SC(=S)N(CC(=O)O)C3=O)o2)c([N+](=O)[O-])c1] | ESI (m/z): 435(M+) |
| 21 | 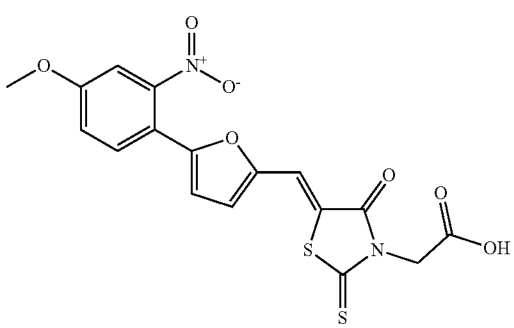 [SMILES: COc1ccc(-c2ccc(/C=C3\SC(=S)N(CC(=O)O)C3=O)o2)c([N+](=O)[O-])c1] | ESI (m/z): 421(M+) |
| 22 | 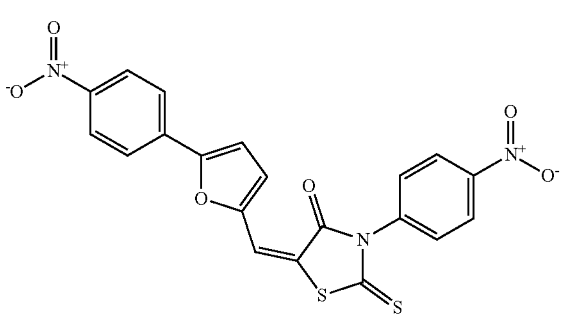 | ESI (m/z): 454(M+) |

TABLE 1-continued
| Example | Structure | LC-MS (M+ H) data or <br>¹H NMR data |
|---|---|---|
| 23 | 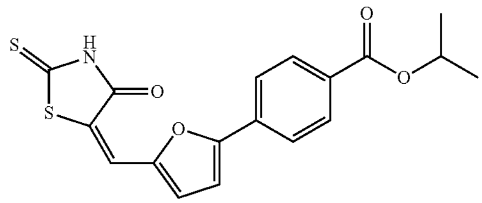 [SMILES: CC(C)OC(=O)c1ccc(-c2ccc(/C=C3/SC(=S)NC3=O)o2)cc1] | ESI (m/z): 374(M+) |
Examples 24 to 38
The same procedure as in Example 1 was carried out to prepare compounds of Examples 24 to 38. Structural formulas of the compounds of Examples 24 to 38 are summarized in Table 2, below.
TABLE 2
| Example | Structure |
|---|---|
| 24 | 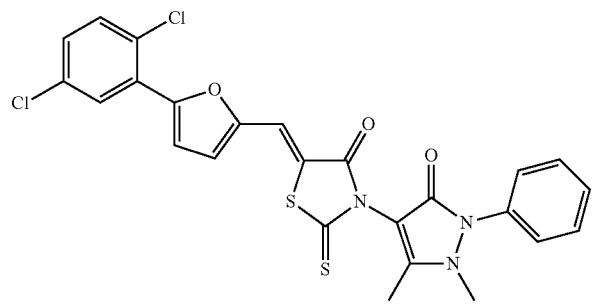 [SMILES: Cc1c(N2C(=O)/C(=C/c3ccc(-c4cc(Cl)ccc4Cl)o3)SC2=S)c(=O)n(-c2ccccc2)n1C] |
| 25 | 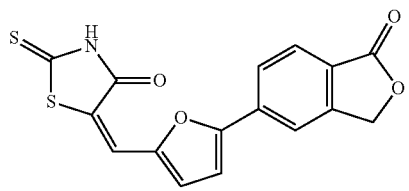 [SMILES: O=C1NC(=S)S/C1=C/c1ccc(-c2ccc3c(c2)COC3=O)o1] |
| 26 | 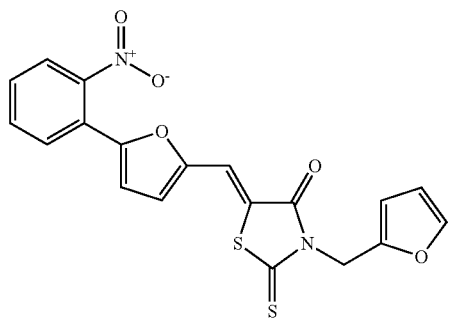 [SMILES: O=C1/C(=C/c2ccc(-c3ccccc3[N+](=O)[O-])o2)SC(=S)N1Cc1ccco1] |

TABLE 2-continued

| Example | Structure |
|---|---|
| 27 | 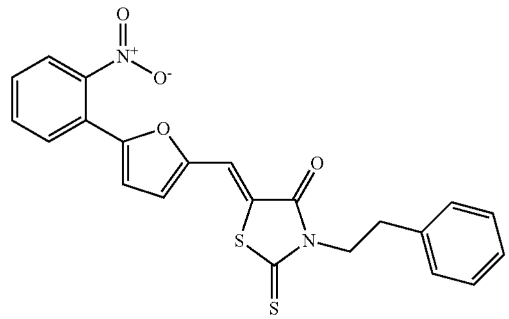 [SMILES: O=C1/C(=C/c2ccc(-c3ccccc3[N+](=O)[O-])o2)SC(=S)N1CCc1ccccc1] |
| 28 | 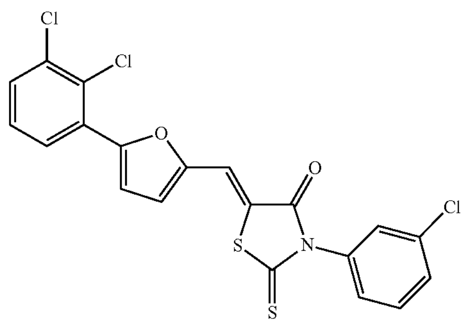 [SMILES: O=C1/C(=C/c2ccc(-c3cccc(Cl)c3Cl)o2)SC(=S)N1c1cccc(Cl)c1] |
| 29 | 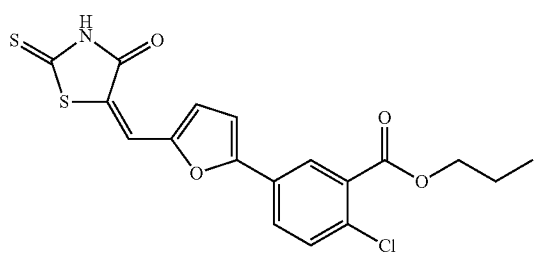 [SMILES: CCCOC(=O)c1cc(-c2ccc(/C=C3/SC(=S)NC3=O)o2)ccc1Cl] |
| 30 | 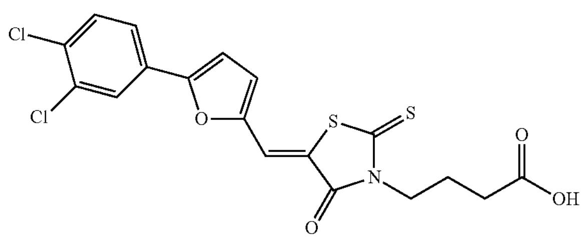 [SMILES: O=C(O)CCCN1C(=O)/C(=C/c2ccc(-c3ccc(Cl)c(Cl)c3)o2)SC1=S] |
| 31 | 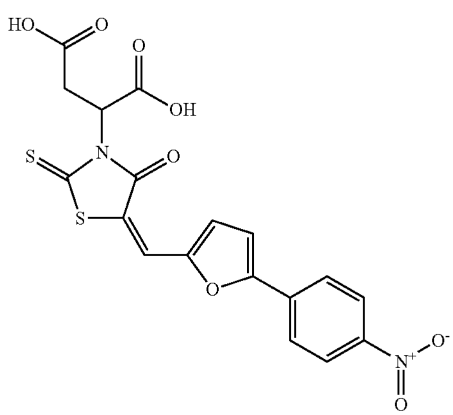 [SMILES: O=C(O)CC(C(=O)O)N1C(=O)/C(=C\c2ccc(-c3ccc([N+](=O)[O-])cc3)o2)SC1=S] |

TABLE 2-continued

| Example | Structure |
|---|---|
| 32 | 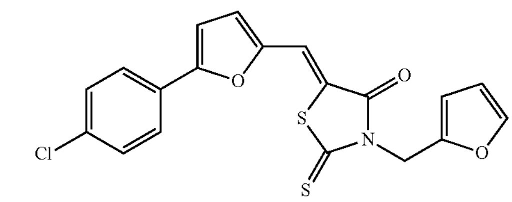 [SMILES: O=C1/C(=C/c2ccc(-c3ccc(Cl)cc3)o2)SC(=S)N1Cc1ccco1] |
| 33 | 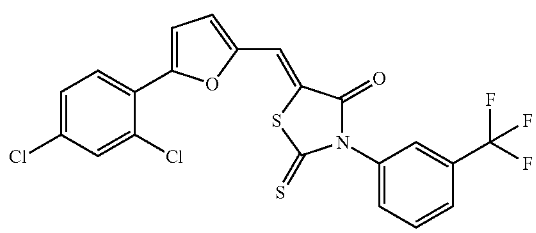 [SMILES: O=C1/C(=C/c2ccc(-c3ccc(Cl)cc3Cl)o2)SC(=S)N1c1cccc(C(F)(F)F)c1] |
| 34 | 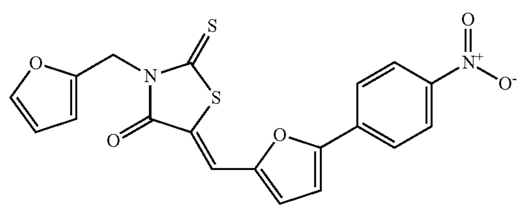 [SMILES: O=C1/C(=C/c2ccc(-c3ccc([N+](=O)[O-])cc3)o2)SC(=S)N1Cc1ccco1] |
| 35 | 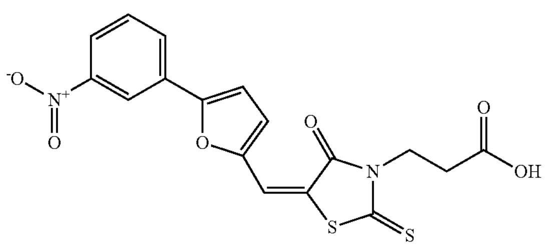 |
| 36 | 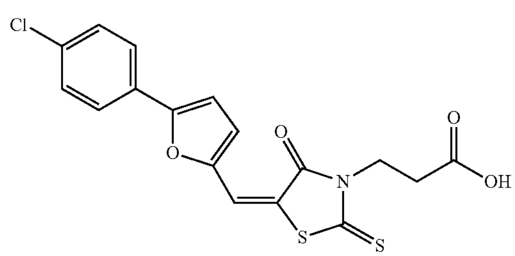 [SMILES: O=C(O)CCN1C(=O)/C(=C\c2ccc(-c3ccc(Cl)cc3)o2)SC1=S] |
| 37 | 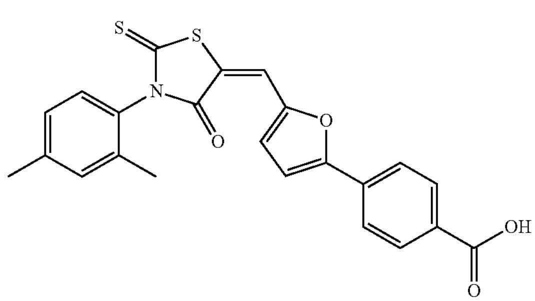 [SMILES: Cc1ccc(N2C(=O)/C(=C\c3ccc(-c4ccc(C(=O)O)cc4)o3)SC2=S)c(C)c1] |

TABLE 2-continued

| Example | Structure |
|---------|-----------|
| 38 | (structure: rhodanine derivative with N-CH2-COOH, S=C, and 5-(3-nitrophenyl)furan-2-ylmethylene substituent) |

Experimental Example 1

Assay for Inhibitory Activity of the Rhodanine Derivatives Against HIV

The rhodanine derivatives of the present invention were assayed for inhibitory activity against HIV as follows.

1. Preparation of HIV

A pNL4-3 vector carrying an HIV genome was transduced into 293FT cells. The HIV genome on pNL4-3 does not infect the body because it contains an EGFP gene in substitution for the nef. 293FT cells were seeded at a density of $3.0\times10^5$ cells/well into 6-well plates containing antibiotic-free DMEM supplemented with 10% FBS and grown for 48 hrs. Upon 90-95% confluency, the transduction was performed.

The DNA (pNL4-3) was added at a final concentration of 10 ng/mL to 250 μL of the reduced serum medium Opti-MEM I (GIBCO™, USA). Separately, 4 μL of Lipofectamine™ 2000 (Invitrogen, USA) was mixed with 250 μL of Opti-MEM I (GIBCO™), and incubated at room temperature for 5 min. The DNA (pNL4-3) was mixed at a ratio of 1:2 with the lipofectamine and reacted at room temperature for 20 min to form a DNA-lipofectamine complex. After removal of the medium from the cell culture, the mixture containing the DNA-lipofectamine complex was added to the cells and incubated for 4 hrs in a $CO_2$ incubator. Then, the cell culture medium was replaced with a fresh antibiotic-free, 10% FBS-supplemented DMEM, followed by incubation for an additional 48 hrs. The HIV-infected cell culture was centrifuged at 1,500 rpm for 5 min to give a virus supernatant.

MT-4 cells were plated at a density of $1.0\times10^6$ cells/mL into 6-well plates containing RPMI supplemented with 10% FBS and incubated for 4 hrs before infection at a ratio of 1:1 with the virus supernatant. The cells were incubated for 48 hrs in a $CO_2$ incubator, after which the culture medium was replaced with a fresh one. Again, incubation was continued for an additional 72 hrs to amplify the virus. After centrifugation at 1,500 rpm for 5 min, the virus supernatant thus obtained was examined for virus density using a Vironostika HIV-1 Antigen Microelisa system kit (bioMerieux, Inc. Netherland).

2. Assay for Inhibitory Activity Against HIV

The rhodanine derivatives prepared in Examples 1 to 38 were dissolved in DMSO to prepare respective 10 mM or 20 mM stocks, and stored at −20° C. The stocks were diluted to a starting concentration of 200 μM in DMSO before use in experiments.

MT-4 cells were suspended at a density of $4\times10^5$ cells in 200 μL of RPMI 1640 (Gibco, 10% FBS) per well of 24-well plates, and infected with 200 μL of a virus supernatant containing $2\times10^5$ pg/mL to give a total volume of 400 μL. After the stocks of the rhodanine derivatives were 10-fold diluted to 200 μM in DMSO, 2 μL of each dilution was added to the cells to a final concentration of 1 μM or less. For a positive control, 10 μM AZT (azidothymidine, Sigma, USA) was used at a final concentration of 50 nM while DMSO was used at a final concentration of 0.5% as a negative control. The cells were cultured for 48 hrs in a $CO_2$ incubator (37° C., 5% $CO_2$), and the culture medium was replaced by RPMI 1640 containing the rhodanine derivative at a final concentration of 1 μM, followed by incubation for an additional 48 hrs. Virus soups were separated from cells by centrifugation at 1,500 rpm for 5 min and then at 13,000 rpm for 5 min. ELISA for p24 concentrations was carried out using a Vironostika HIV-1 Antigen Microelisa system kit (bioMerieux, Inc. Netherland) to determine the inhibitory activity of each of the rhodanine derivatives against HIV.

Anti-HIV activities (μM) of the rhodanine derivatives of the present invention are summarized in Table 3, below.

TABLE 3

| Example No. | Conc. for Inhibition of HIV Activity ($IC_{50}$) |
|---|---|
| 1 | 0.8 μM |
| 5 | 1.0 μM |
| 8 | 0.5 μM |
| 13 | 0.5 μM |
| 16 | 0.5 μM |
| 21 | 1.0 μM |
| 23 | 0.4 μM |
| 29 | 0.5 μM |
| 38 | 0.75 μM |
| Positive Control (AZT) | 0.005 μM |

As can be seen in Table 3, the rhodanine derivatives of the present invention exhibited high inhibitory activity against HIV.

Formulation examples are given to illustrate dosage preparations containing the composition of the present invention.

Formulation Example 1

Preparation of Powder

Rhodanine Derivative of the present invention 0.1 g

Lactose 1.5 g

Talc 0.5 g

These ingredients were mixed and loaded into an airtight sac to give a powder.

Formulation Example 2

Preparation of Tablet

Rhodanine Derivative of the present invention 0.1 g
Lactose 7.9 g
Crystalline cellulose 1.5 g
Magnesium stearate 0.5 g These ingredients were mixed and directly compressed into a tablet.

Formulation Example 3

Preparation of Capsule

Rhodanine Derivative of the present invention 0.1 g
Corn starch 5 g
Carboxycellulose 4.9 g These ingredients were admixed together and the admixture was loaded into a conventional capsule using a suitable device.

Formulation Example 4

Preparation of Injection

Rhodanine Derivative of the present invention 0.1 g
Sterile water for injection suitable amount
pH Adjuster suitable amount
Stabilizer suitable amount Using a conventional method, these ingredients were put into an ampule (2 ml) to give an injection.

Formulation Example 5

Preparation of Liquid Medicine

Rhodanine Derivative of the present invention 0.1 g
Isomerized sugar 10 g
Mannitol 5 g
Purified water suitable amount Each ingredient was dissolved in purified water and flavored with lemon before admixing together. Purified water was added to the admixture to form a final volume of 100 ml which was then loaded into a brown vial and sterilized.

INDUSTRIAL APPLICABILITY

As described hitherto, the rhodanine derivatives of the present invention inhibit HIV virus expression, thus finding applications in the prevention or treatment of AIDS.

The invention claimed is:

1. A Rhodanine derivative, selected from the group consisting of:
   3-(2-methanesulfonyl-ethyl)-5-[5-(3-nitro-phenyl)-furan-2-ylmethylene]-2-thioxo-thiazolidin-4-one,
   5-[5-(4-bromo-phenyl)-furan-2-ylmethylene]-3-(3-oxo-butyl)-2-thioxo-thiazolidin-4-one,
   5-(naphthalen-1-yl-furan-2-ylmethylene)-3-(2-oxo-propyl)-2-thioxo-thiazolidin-4-one, and
   5-[5-(2-nitro-phenyl)-furan-2-ylmethylene]-3-(4-oxo-pentyl)-2-thioxo-thiazolidin-4-one,
   or
   a pharmaceutically acceptable salt of any of the foregoing compounds.

2. A method for preparing a rhodanine derivative of Chemical Formula 1, comprising:
   reacting an amine compound of Chemical Formula 2 with carbon disulfide ($CS_2$) and bromoacetic acid to synthesize a compound of Chemical Formula 3,
   reacting a halide compound of Chemical Formula 4 with 5-formyl-2-furanboronic acid to synthesize a compound of Chemical Formula 5, and
   reacting the compound of Chemical Formula 3 synthesized in step 1), with the compound of Chemical Formula 5 synthesized in step 2), to synthesize a compound of Chemical Formula 1, as illustrated in the following Schematic Scheme 1:

[Reaction Scheme 1]

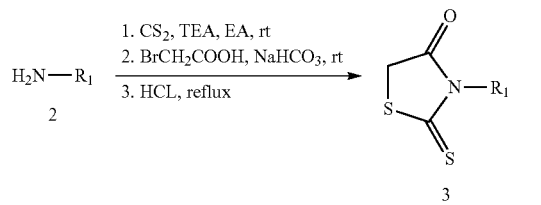

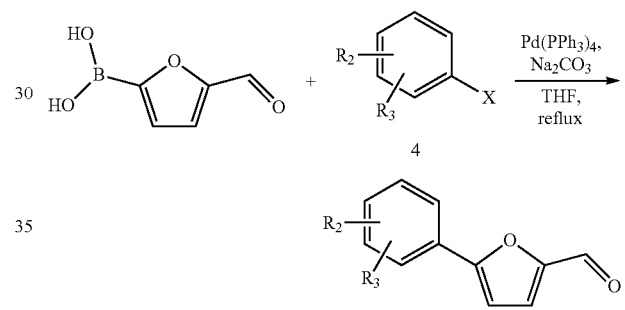

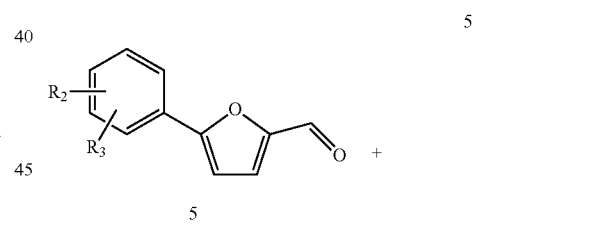

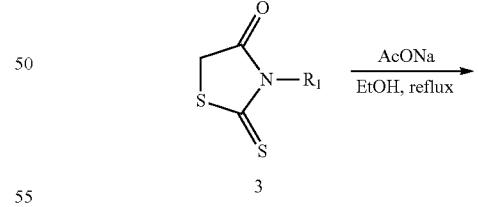

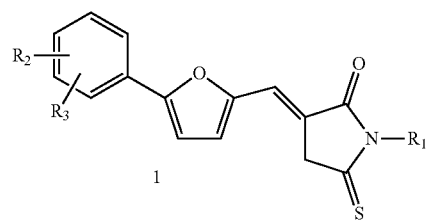

wherein,

R$_1$ is H, ethyl, cyclohexyl, —(CH$_2$)n-A-B, —(CH$_2$)m-phenyl, 2,4-dimethylphenyl,

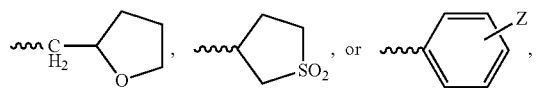

Wherein
A is (C=O) or SO$_2$,
B is methyl or hydroxy,
Z is F, I, NO$_2$, CF$_3$, or —N(CH$_2$CH$_3$)$_2$,
n is an integer of 1~3, and
m is an integer of 1 or 2,
R$_2$, and R$_3$, which may be the same or different, are independently H, NO$_2$, Br, Cl, methyl, methoxy, ethoxy, —(C=O)—O—CH(CH$_3$)$_2$, or morpholine, or R$_2$ and R$_3$ are positioned ortho to each other, joining together to form

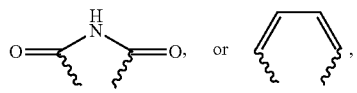

and
X is a halogen atom.

3. A method of inhibiting HIV in a subject comprising:
administering to the subject in need thereof a rhodanine derivative selected from the group consisting of:
3-(2,4-dimethyl-phenyl)-5-[5-(3-nitro-phenyl)-furan-2-ylmethylene]-2-thioxo-thiazolidin-4-one,
5-[5-(4-bromo-phenyl)-furan-2-ylmethylene]-3-(3-oxo-butyl)-2-thioxo-thiazolidin-4-one,
5-[5-(2,4-dichloro-phenyl)-furan-2-ylmethylene]-3-(3-fluoro-phenyl)-2-thioxo-thiazolidin-4-one,
3-(3-fluoro-phenyl)-5-[5-(4-nitro-phenyl)-furan-2-ylmethylene]-2-thioxo-thiazolidin-4-one,
5-[5-(2-bromo-5-nitro-phenyl)-furan-2-ylmethylene]-3-(4-iodo-phenyl)-2-thioxo-thiazolidin-4-one,
{5-[5-(4-methoxy-2-nitro-phenyl)-furan-2-ylmethylene]-4-oxo-2-thioxo-thiazolidin-3-yl}-acetic acid,
4-[5-(4-oxo-2-thioxo-thiazolidin-5-ylidene methyl)-furan-2-yl]-benzoic acid isopropylester, and
2-chloro-5-[5-(4-oxo-2-thioxo-thiazolidin-5-ylidene methyl)-furan-2-yl]-benzoic acid propyl ester,
or
a pharmaceutically acceptable salt of any of the foregoing compounds.

4. The Rhodanine derivative of claim 1, which is 3-(2-methanesulfonyl-ethyl)-5-[5-(3-nitro-phenyl)-furan-2-ylmethylene]-2-thioxo-thiazolidin-4-one or a pharmaceutically acceptable salt thereof.

5. The Rhodanine derivative of claim 1, which is 5-[5-(4-bromo-phenyl)-furan-2-ylmethylene]-3-(3-oxo-butyl)-2-thioxo-thiazolidin-4-one or a pharmaceutically acceptable salt thereof.

6. The Rhodanine derivative of claim 1, which is 5-(naphthalen-1-yl-furan-2-ylmethylene)-3-(2-oxo-propyl)-2-thioxo-thiazolidin-4-one or a pharmaceutically acceptable salt thereof.

7. The Rhodanine derivative of claim 1, which is 5-[5-(2-nitro-phenyl)-furan-2-ylmethylene]-3-(4-oxo-pentyl)-2-thioxo-thiazolidin-4-one or a pharmaceutically acceptable salt thereof.

8. The method of claim 3, wherein the rodanine derivative is 3-(2,4-dimethyl-phenyl)-5-[5-(3-nitro-phenyl)-furan-2-ylmethylene]-2-thioxo-thiazolidin-4-one or a pharmaceutically acceptable salt thereof.

9. The method of claim 3, wherein the rodanine derivative is 5-[5-(4-bromo-phenyl)-furan-2-ylmethylene]-3-(3-oxo-butyl)-2-thioxo-thiazolidin-4-one or a pharmaceutically acceptable salt thereof.

10. The method of claim 3, wherein the rodanine derivative is 5-[5-(2,4-dichloro-phenyl)-furan-2-ylmethylene]-3-(3-fluoro-phenyl)-2-thioxo-thiazolidin-4-one or a pharmaceutically acceptable salt thereof.

11. The method of claim 3, wherein the rodanine derivative is 3-(3-fluoro-phenyl)-5-[5-(4-nitro-phenyl)-furan-2-ylmethylene]-2-thioxo-thiazolidin-4-one or a pharmaceutically acceptable salt thereof.

12. The method of claim 3, wherein the rodanine derivative is 5-[5-(2-bromo-5-nitro-phenyl)-furan-2-ylmethylene]-3-(4-iodo-phenyl)-2-thioxo-thiazolidin-4-one or a pharmaceutically acceptable salt thereof.

13. The method of claim 3, wherein the rodanine derivative is {5-[5-(4-methoxy-2-nitro-phenyl)-furan-2-ylmethylene]-4-oxo-2-thioxo-thiazolidin-3-yl}-acetic acid or a pharmaceutically acceptable salt thereof.

14. The method of claim 3, wherein the rodanine derivative is 4-[5-(4-oxo-2-thioxo-thiazolidin-5-ylidene methyl)-furan-2-yl]-benzoic acid isopropylester or a pharmaceutically acceptable salt thereof.

15. The method of claim 3, wherein the rodanine derivative is 2-chloro-5-[5-(4-oxo-2-thioxo-thiazolidin-5-ylidene methyl)-furan-2-yl]-benzoic acid propyl ester or a pharmaceutically acceptable salt thereof.

* * * * *